United States Patent [19]
Tsang et al.

[11] Patent Number: 5,354,660
[45] Date of Patent: Oct. 11, 1994

[54] ISOLATION OF DIAGNOSTIC GLYCOPROTEINS TO TAENIA SOLIUM, IMMUNOBLOT-ASSAY AND METHOD FOR THE DETECTION OF HUMAN CYSTICERCOSIS

[75] Inventors: Victor C. W. Tsang, Decatur; Joy A. Brand, Atlanta; Anne E. Boyer; Marianna Wilson, both of Decatur; Peter M. Schantz, Atlanta; Shirley E. Maddison, Decatur, all of Ga.

[73] Assignee: The United States of America as represented by the Secretary of the Department of Health and Human Services, Washington, D.C.

[21] Appl. No.: 863,486

[22] Filed: Apr. 2, 1992

Related U.S. Application Data

[63] Continuation of Ser. No. 292,393, Dec. 30, 1988, abandoned.

[51] Int. Cl.$^5$ .................. G01N 33/569; G01N 33/53
[52] U.S. Cl. ............................... 435/7.22; 435/7.2; 435/7.22; 435/7.92; 435/34; 435/174; 435/179; 435/810; 435/805; 436/526; 436/518; 436/530; 436/543; 436/808; 436/811; 436/809
[58] Field of Search ...................... 435/7.2, 7.22, 7.92, 435/34, 174, 179, 810, 805; 436/501, 516, 518, 530, 543, 63, 808, 811, 809

[56] References Cited

U.S. PATENT DOCUMENTS

| | | | |
|---|---|---|---|
| 4,562,160 | 12/1985 | Real et al. | 436/518 |
| 4,725,406 | 2/1988 | Compton et al. | 435/287 |
| 4,740,456 | 4/1988 | Kuhn et al. | 435/7 |
| 4,801,532 | 1/1989 | Kuhn et al. | 435/7 |

OTHER PUBLICATIONS

Joo, K. H. et al, Biological Abstracts, No. 95163, vol. 85, May 1988 (Korea Univ. Med J., 24(3), 1987, 139–150).

Gottstein, B. et al, Biological Abstracts, No. 24341, vol. 82, 1986 (Am. J. Trop. Med. Hyg. 135(2). 1986, 308–313).

Tsang et al, Journal of Immunological Methods, vol. 70, 1984, pp. 91–100.

Garcia, et al., "Diagnosis of Cysticercosis in Endemic Regions," The Lancet, 338, pp. 549–551, 1991.

Diaz, et al., "Immunodiagnosis of Human Cysticercosis (Taenia Solium), " Am. J. Trop. Med. Hyg, 46(5) pp. 610–615, 1992.

Gonzalez, et al., "Prevalence & Comparison of Serologic Assays, Necropsy, and Tongue Examination for the Diagnosis of Porcine Cysticercosis in Peru, "Am. J. Trop. Med. Hyg., 43(2), 1990, pp. 194–199.

Tsang et al., An Enzyme-Linked Immunoelectrotransfer Blot Assay and Glycoprotein Antigens for Diagnosing Human Cysticercosis (Taenie Solium), *The Journal of Infectious Diseases,* vol. 159, No. 1, Jan. 1989.

*Primary Examiner*—Toni R. Scheiner
*Attorney, Agent, or Firm*—Needle & Rosenberg

[57] ABSTRACT

The present invention is directed to a method and a kit for diagnosing active human neurocysticercosis utilizing an immunoblot assay which comprises:

detecting the presence of antibodies in the serum or cerebrospinal fluid of a human to be diagnosed, wherein the antibodies are reacted with *Taenia solium* larval antigens which have been isolated by lentil lectin affinity. The larval antigens are designated GP50, GP42, GP24, GP21, GP18, GP14, and GP13, wherein GP indicates that said antigen is a glycoprotein and the number indicates the molecular weight in K daltons, as determined by SDS-PAGE.

10 Claims, 5 Drawing Sheets

ISOLATION OF DIAGNOSTIC GLYCOPROTEINS TO TAENIA SOLIUM, IMMUNOBLOT-ASSAY AND METHOD FOR THE DETECTION OF HUMAN CYSTICERCOSIS

This application is a continuation, of application Ser. No. 07/292,393 filed on Dec. 30, 1988, now abandoned.

BACKGROUND OF THE INVENTION

1. Field of the Invention

The present invention relates to an immunoblot enzyme immuno transferable assay useful for diagnosing human cysticercosis.

2. Background of the Invention

Human cysticercosis is a potentially fatal invasion of various tissues by the larvae of *Taenia solium*. The disease has increased dramatically in prominence as a medical problem in the United States since 1977. Increased travel and immigration from highly endemic areas such as Mexico and Central America make recognition and treatment of cysticercosis a U.S. public health priority. The impetus to develop a more sensitive and specific immunodiagnostic test for human cysticercosis, was provided by the increasing demands for a confirmatory assay to support clinical and radiological findings and by the effectiveness of Praziquantel for the treatment of cysticercosis.

Previous efforts to improve serodiagnostic assays have concentrated on the ELISA (enzyme-linked immunoabsorbent assay), IHA (indirect hemagglutinatino assay), and RIA (radioimmmunoassay) formats. Claimed test efficacy for these assays ranged from 67%–100% specificity and 47%–95% sensitivity. Many reports, however, based their claims on relatively low serum sample numbers, and frequency of cross-reactivity from heterologous infections, such as Echinococcus spp., was not addressed. In general, the prior art seriologic assays for human cysticercosis lack either specificity or sensitivity, or in some cases both specificity and sensitivity.

U.S. Pat. No. 4,740,456 discloses an immunological method for diagnosing neurocysticercosis which involves detecting antigens of larval origin. The antigens to be assayed are selected from those antigens identified having molecular weights of 64K, 53K and 30–32K. daltons as determined by sodium dodecyl polyacrylamide gel electophoresis (SDS-PAGE). The preferred method of antigen detection is by way of the ELISA method. The method to date has not been utilized in the diagnosis of neurocysticercosis due to its many drawbacks such as lack of sensitivity and specificity.

With respect to the kit utilized in the diagnosis, of the Kuhn patent, i.e., the disc method, reaction with one particular antigen cannot be distinguished from that of the other antigens. Furthermore, the discs are only antigen coated and thus the antigens are not tightly bound to the disc. The above disadvantages result in a loss of specificity and sensitivity of the diagnosis. The present invention has been accomplished with the above disadvantages in mind.

SUMMARY OF THE INVENTION

It is therefore an object of the invention to provide an immunoblot assay, or, an EITB enzyme linked immunoelectrotransfer blot assay for the detection of human cysticercosis.

Further, the invention is directed to the isolation of the diagnostic glycoproteins of *Taenia solium* which are used in the above-described assay.

Moreover, the invention is directed to a method for the serological detection of human cysticercosis utilizing an immunoblot assay which, unlike the prior art assays, is useful for diagnosing human cysticercosis and which is 98% sensitive and 100% specific. The method comprises the steps of detecting the presence of antibodies in the serum or cerebrospinal fluid of a human to be diagnosed, wherein said antibodies are reactive with at least one *Taenia solium* larval antigen which has been isolated by lentil lectin affinity chromatography, at least one of said lentil lectin purified glycoproteins being selected from the group consisting of GP50, GP42, GP24, GP21, GP18, GP14, and GP13, wherein GP indicates that said antigen is a glycoprotein and the number indicates the molecular weight in K daltons, as determined by SDS-PAGE.

The method preferably comprises the steps of the method of claim 1, which comprises locally and separately immobilizing all seven of the glycoproteins on a matrix, contacting the immobilized glycoproteins with serum or cerebrospinal fluid of a human to be diagnosed to react antibodies in the cerebrospinal fluid with the glycoproteins; and determining whether the antibodies have reacted with the glycoproteins.

A further object of the invention is the a kit used in diagnosing human cysticercosis in both serum and cerebral spinal fluid from patients who are to be diagnosed. The kit comprises a matrix strip, having electrophoretically bonded directly to said matrix separate and distinct integral bands of the following lentil lectin isolated glycoproteins GP50, GS42, GP24, GP21, GP18, GP14 and GP13, one or more of which are reactive with antibodies in the human serum or cerebrospinal fluid; and a housing for developing said matrix strips. The matrix material can be nylon or DAB paper but is preferably nitrocellulose.

These and other objects of the invention will become more apparent upon reading the specification to which the invention is described in detail.

DESCRIPTION OF THE PREFERRED EMBODIMENTS

The first object to be accomplished by the present invention is the diagnosis of human cysticercosis. The object is accomplished by utilizing an immunoblot or EITB assay specific to isolated antigens to *T. Solium*. The procedure requires preparation of the antigens to be utilized, SDS treatment and optimization of antigen, and running an immunoblot or EITB assay on samples obtained from either the serum or the cerebrospinal fluid of patients.

The present invention is directed to a method for diagnosing human cysticercosis utilizing an immunoblot assay consisting essentially of detecting the presence of antibodies in the serum or cerebrospinal fluid of a human to be diagnosed, wherein said antibodies are shown to be reactive with at least one lentil lectin isolated *Taenia solium* larval glycoprotein antigens and wherein said lentil lectin isolated glycoproteins are selected from the group consisting of GP50, GP42, GP24, GP21, GP18, GP14, and GP13, wherein GP stands for glycoprotein and the number indicates the molecular weight of the lentil lectin glycoprotein in terms of K daltons, as determined by SDS-PAGE.

The invention is also directed to kits which are utilized in the diagnosis of human cysticercosis from human serum or cerebrospinal fluid from a patient to be diagnosed. The kit consists of nitrocellulose strips wherein each specific Lentil lectin glycoprotein antigenic bands is distinctly separated as integrals along the nitrocellulose strips. Unlike U.S. Pat. No. 4,740,456, reaction to one band can be easily differentiated from reaction with other bands. Such integral and distinct separation provides a kit which results in increased specificity, and no possibility of misinterpretation of results from cross-reactions with irrelevant antigens.

The procedures for preparation of the antigens, immunoblot assay and kit will be described in detail hereinbelow.

All chemicals were reagent grade or better. Unless specified otherwise, they were obtained from Mallinckrodt Inc., St. Louis, Mo. Tris, sucrose, urea, and ammonium sulfate in ultra pure grade were obtained from Schwarz/Mann, Inc., Orangeburg, N.Y. All goat anti-Ig-POD (anti-human IgG=heavy and light chain specific; POD=horseradish peroxidase, donor: $H_2O_2$ oxidoreductase, EC 1.11.17) reagents are prepared by immunoaffinity with IgG: POD molar ratios ranging from 1:2.8 to 1:3.4 from the procedures set forth in Tsang et al. Quantitative Capacities of Glutaraldehyle and Sodium m. periodate Coupled Peroxidase-Anti-Human IgG Cojugates in Enzyme-Linked Assays, J. Immunol Methods 70:91-100 (1984). All percentage herein are by weight unless otherwise specified.

Three serum pools, *T. solium* (TSP); Echinococcus ssp. (EC), and normal human serum (NHS) were prepared to serve as antibody reagents. TSP was formed by pooling equal volumes of serum from 7 persons with parasitologically (histologically) confirmed cysticercosis. These 7 sera were selected for their ability to react with the maximum number of antigen bands in EITB against crude *T. solium* cysticerci antigens. The serum pool EC was composed of equal volumes of 4 sera from parasitologically confirmed cases of *Echinococcus granulosus* or *Echinococcus multilocularis* infections. NHS was a pool of sera derived from 50 healthy U.S. residents who never traveled to endemic areas. All serum pools (TSP, EC, and NHS), when used as antibody reagents in assay for antigen efficacies, were present in excess.

All individual serum samples used in the study were selected on the basis of parasitological confirmation. Every effort was made to include individual serum associated with a single disease. In selecting serum from patients with heterologous infections, safeguards were made against the possibility of concommitant *T. solium* infection by including only serum from *T. solium*-free geographic locations. All *T. solium* cysticercosis infected serum were collected from surgically confirmed cases. Documentation was individually confirmed through the patient's physician or hospital pathologist. Only cases with either clear histological or gross morphological evidence are considered as positive *T. solium* infections. Documentation for all other serum was previously reported in J Immunol, 130:1366-1370 (1983). All serum and CSF samples are listed in Table I below.

TABLE I

| EITB RESULTS OF SERUM OR CSF[1] | | |
|---|---|---|
| DISEASES (OR PATHOGENS)[1] | POSITIVES | NEGATIVES |
| CYSTICERCOSIS (*T. solium*): | | |
| SERUM | 108 | 3 |
| CSF | 37 | 0 |
| AMEBIASIS | 0 | 24 |
| ASCARIASIS | 0 | 5 |
| *Brugia malayi* | 0 | 3 |
| CLONORCIASIS | 0 | 29 |
| *Echinococcus granulosus* | 0 | 18 |
| *Echinococcus multilocularis* | 0 | 16 |
| *Fasciola hepatica* | 0 | 8 |
| HEPATITIS | 0 | 30 |
| ONCHOCERCIASIS | 0 | 105 |
| PARAGONIMIASIS | 0 | 21 |
| SCHISTOSOMIASIS (ALL SPECIES) | 0 | 87 |
| *Strongyloides spp.* | 0 | 3 |
| *Treponema pallidum* | 0 | 14 |
| *Trichinella spirallis* | 0 | 8 |
| *Wuchereria brancrofti* | 0 | 5 |
| UNINFECTED SERUM[2] | 0 | 45 |
| HETEROLOGOUS INFECTION CSF[3] | 0 | 9 |

[1]Cysticercosis infections n = 148
Heterologous infections n = 376
Healthy controls n = 54
TOTAL SAMPLES TESTED n = 578
All infections were confirmed by presence of organisms.
Serum tested at 1:50 and CSF at 1:10 dilution.
[2]From healthy U.S. residents who have never traveled abroad.
[3]From patients with mycotic diseases

EXAMPLE 1

Preparation of LL-GP Antigens

Figure 1:
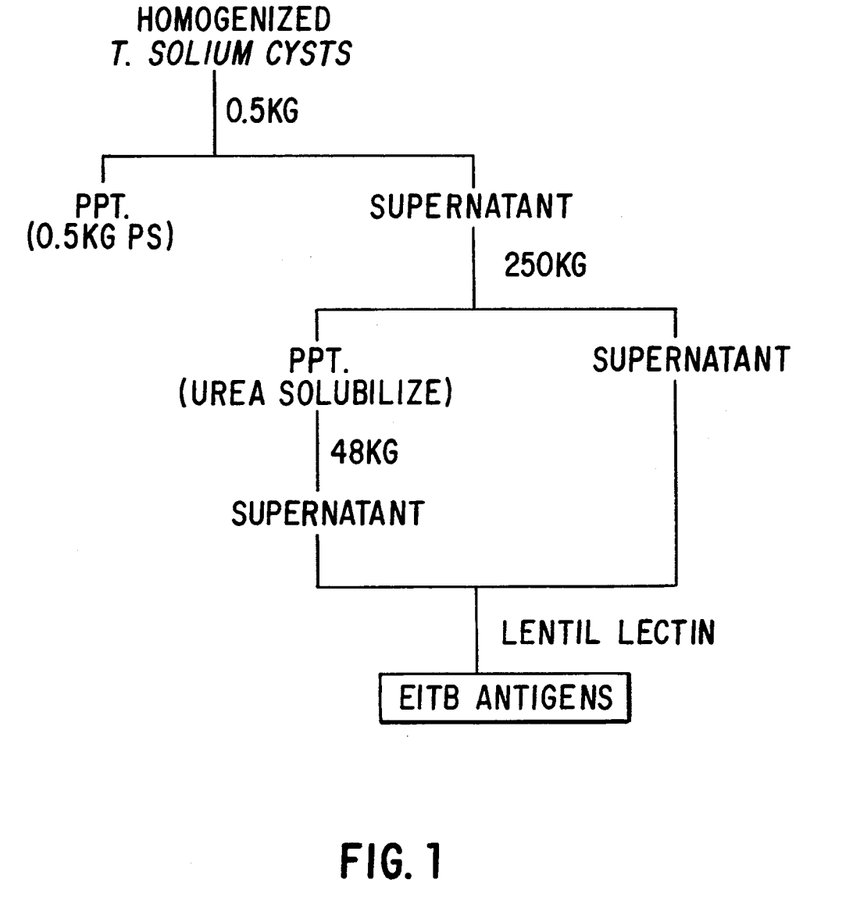
FIG. 1 is a schematic for *T. solium* antigen fractionation. EITB antigens=LL-GP. Lentil lectin chromatography was conducted at 25° C., all other procedures were performed at 4° C.

The schematic for the production of antigens for EITB appears in FIG. 1. Frozen (liquid $N_2$ temperatures) cysts, in 1 to 20 g lots, were quickly thawed in 5 volumes (1/5 w/v of sucrose/HEPES/PMSF buffer (0.05M HEPES-NaOH, 0.25M sucrose, 2.0 mM EDTA, 5 mM PMSF, pH 7.20) at 37° C. PMSF (phenylmethysulfonyl fluoride), or benzyl sulfonyl fluotride both obtained from Calbilchem, La Jolla, Calif. was incorporated into buffers to a final concentration of 5 mM. Because of the lability of PMSF to hydrolysis in aqueous solutions at a pH$\leq$7.00, in all instances where PMSF was included, the following procedure was used: A stock solution of 100 mM PMSF in absolute isopropanol (2-propanol) was maintained at $-20°$ C. Just before use, the 100 mM PMSF was heated in a microwave oven for approximately 30 sec to dissolve any crystallized PMSF. The buffer to be incorporated with PMSF was also heated in a microwave to about 50° C. Stock PMSF (100 mM) was then slowly added to yield a final concentration 5 mM. The final buffer with PMSF was then quickly chilled to 4° C. in an ice-water bath. Without exception, the expiration time for the final buffer with 5 mM PMSF was rigidly set to 20 min. In most instances, all buffers with 5 mM PMSF were used within 10 min. Once thawed, the suspension of cysts in buffer was quickly chilled to 4° C. with ice/water mixtures. Unless specified otherwise, all procedures henceforth were conducted at 4° C. Cyst suspensions were homogenized by a Polytron homogenizer equipped with a PT-20 ST probe (Brinkmann Instruments, Inc., Westbury, N.Y.). Homogenization was accomplished in two 1-min pulses with the probe speed set at 6 and the pulses separated by a 2-min pause for sample cooling. The homogenate was centrifuged at 500×G for 20 min. A white floating pellet followed by a large, cloudy supernatant with a pink, loose bottom pellet was the result of this initial centrifugation. The cloudy supernatant was carefully removed with a syringe and 14 gauge cannula, and the floating pellet was allowed to settle onto the side of the centrifuge tube or the bottom pellet. The combined pellet was again homogenized and centrifuged as before in an additional 5 volumes of sucrose/HERPES/PMSF buffer. The size of the floating pellet generally decreased greatly with the second homogenization and centrifugation. The supernatant from the second centrifugation was combined with that of the first and was designated the 0.5 KG supernatant, while the twice-extracted pellet was named 0.5 KG ppt. The 0.5 KG supernatant was centrifuged at 250 KG for 2 hr, yielding a dense pellet and a clear supernatant. The lipid scum on top of the supernatant was carefully aspirated, and adherent residues were also removed with a cotton swab.

The 250 KG pellet was suspended in 10 to 20 ml of urea/PMSF buffer (8M urea, 0.05M Tris-HCl, 5 mM PMSF, pH 8.00) by gentle repeated passage through a 13 gauge cannula and syringe. The suspended pellets were sonicated at 100% power, 20% pulse duty cycle for 5 min with a Heat Systems sonicator model 275 (Heat Systems, Plain View, N.Y.) equipped with a standard (12.5 mm) horn. The sonicated suspensions were gently stirred with 10 ml of freon TF 130 (Miller-Stephenson, Danbury, Conn.) for 30 min at 4° C. The freon extracted lipid and a small amount of lipoprotein from these samples. The urea extract was centrifuged at 48 KG for 20 min. The pellet was discarded and the supernatant was desalted through a Sephadex G25 Medium (Pharmacia Fine Chemicals, Piscataway, N.J.) column equilibrated with 0.2M NaCl, 0.05M Tris-HCl, pH 8.00 (NaCl/Tris). This desalted fraction was named 250 KG PS.

The 250 KG supernatant was concentrated by ultrafiltration through a YM-10 membrane (Amicon, Danvers, Mass.) desalted with G25 into NaCl/Tris, and named 250 KG SUP. These 2 fractions: 250 KG PS and 250 KG SUP were combined to form a single fraction called LL-P. A lentil lectin Sepaharose 4B (Pharmacia) column was equilibrated with NaCl/Tris. The size of this column was determined by the amount of total protein to be fractionated; 1 ml of lectin gel was prepared for every 3 mg of protein. Before use, lectin columns were first purged with 2 alternating cycles of the base line buffer (NaCl/Tris), and the highest concentration elution buffer (0.2M alpha-methyl-mannoside, 0.2M NaCl, 0.05M Tris-HCl, pH 8.00). Samples equilibrated in NaCl/Tris base line buffer were loaded (ascending) and unbound materials were purged through with 6 to 8 bed volumes of NaCl/Tris. The unbound fraction was named LL-0.00M. Lentil lectin bound glycoproteins were eluted stepwise, first with 5 bed volumes of 0.05M and then with 0.20M solutions of alpha-methyl-mannoside in 0.2M NaCl, 0.05M Tris-HCl, pH 8.00. The fraction with 0.20M alpha-methyl-mannoside, which contained glycoproteins and served as the final antigen for the EITB assay for the present invention, was designated LL-GP. Concentration, where needed, was again accomplished by ultrafiltration through YM-10. The final volume after concentration was determined, and 0.77 volume (0.77×vol. of LL-GP) of glycerol was added and mixed thoroughly. Protein concentrations for LL-GP were determined as per Bradford, Anal Biochem. 72:248-254 (1976). The glycerol diluted LL-GP was divided into aliquots and stored in the vapor phase of liquid $N_2$. The function of glycerol is to protect the antigens from repeated freeze/thaw cycles. Thus, once removed from liquid $N_2$ storage, small unused portions are simply kept at $-20°$ C. At this temperature, LL-GP does not freeze and is stable for months.

EXAMPLE 2

SDS Treatment and Concentration Optimization of Antigens

LL-GP ([protein] between 0.5-0.1 ug/ul) was heated at 65° C. in the presence of 1% SDS, 0.1% bromophenol blue (w/v), 0.01M Tris-HCl, pH 8.00 for 15-20 min. The treated antigens were then diluted with 6% glycerol in water until the final protein concentration was about 0.1 ug/ul, and the SDS concentration was $\leq 0.1\%$. A 2-fold dilution series of the treated antigen was prepared in 0.1% SDS, 0.025% (w/v) bromophenol blue, 1% glycerol, 0.0025M Tris-HCl, pH 8.00. Individual dilutions were applied onto multiwell gels at the rate of 1 ul/mm gel (well) width. Three identical gels were prepared and blotted after SDS-PAGE (sodium dodecyl sulfate polyacrylamide gel electrophoresis). Each of the immunoblots were then exposed to TSP, EC, and NHS, respectively. After the usual development with anti-Ig-POD and substrate, described hereinbelow, the concentration which yielded all 7 clear diagnostic bands with TSP and minimum cross-reactive bands, if any, with EC and NHS was selected as the optimum antigen concentration. The usual optimum concentration for LL-GP when used in the immunoblot assay of the present invention range from 20-80 ng/ul per mm. Details for the preparation of antigens for SDS-PAGE are described in Tsang et al., Methods Enzymol. 92:377-391 (1983) and Tsang et al., Immunology Series No. 15, Procedural Guide; USDHHS, PHS, CDC, Atlanta, Ga. 1986.

EXAMPLE 3

Enzyme-Linked Immunoelectrotransfer Blot (EITB Immunoblot, or "Western Blot"), KIT, Strip Production, and Storage Blots for strip production were usually produced from nitrocellulose, gels (nitrocellulose obtained from Schleicher & Schuell, Keene, N.H. 03431) with a single 130 mm wide sample well. A single line was drawn on the top edge of each blot for orientation. Blots were washed 4 times in PBS/Tween (phosphate buffered saline, 0.10 NaCl, 0.05M $Na_2HPO_4/NaH_2PO_4$, pH 7.20 with 0.3% v/v Tween-20), and twice with PBS. An Accutran ™ cutter was used to separate a single blot (from a 130 mm sample area) into 36 to 44 identical 3 mm strips. Cut strips with resolved antigens are normally stored at $-60°$, covered with a sheet of filter paper saturated with PBS, and at this temperature they are stable for at least 14 months. Strips are also stable at $-4°$ C., however, under this storage condition, they should be in contact with a sheet of filter paper saturated with PBS/Azide (PBS with 0.1% $NaN_3$).

EXAMPLE 4

Serum/CSF Incubation

The assay dilution was 1:50 for serum and 1:10 for CSF. Test samples were diluted with PBS/milk (5.0% nonfat dried milk in PBS) directly into Accutran ™ incubation trays (Schleicher and Schuell, Keen, N.H.). Total volume of diluted sample used per trough was 0.5 ml. One strip was added (blotted surface up) to each sample and the tray gently rocked back and forth to ensure total submersion of the strip. The usual incubation time with serum or CSF was 1 hr, under constant rocking. Incubation of serum with strips may also be allowed to proceed overnight, but the serum dilution should be 1:100. Stored strips were defrosted at 37° C. and were kept moist until use. The strips must not be allowed to dry or emerge above fluid surfaces during incubation, otherwise severe "water marks" may form. Removal of unbound serum components was accomplished with the Accutran ™ washer and warm (56° C.) PBS/Tween. The usual wash consisted of four 5-min washes. After incubating for 1 hr with anti-Ig-POD, strips were washed again for 5 times with PBS/Tween and twice with PBS alone. The conjugates used for this assay should have at least a 1:2 (IgG:POD) molar ratio as described in J. Immunol Method; 70:91–100 (1984). To use conjugates of lower antibody to enzyme ratios is to lessen the sensitivity of this test. Bound antibodies were visualized with DAB (3,3'-diaminobenzidine) substrate solution as described in Tsang et al., Immunology Series No. 15, Procedural Guides, USDHMS, PHS, CDC, Atlanta, Ga. (1986).

EXAMPLE 5

Diagnostic Bands and Interpretation of EITB Results

Figure 2A:
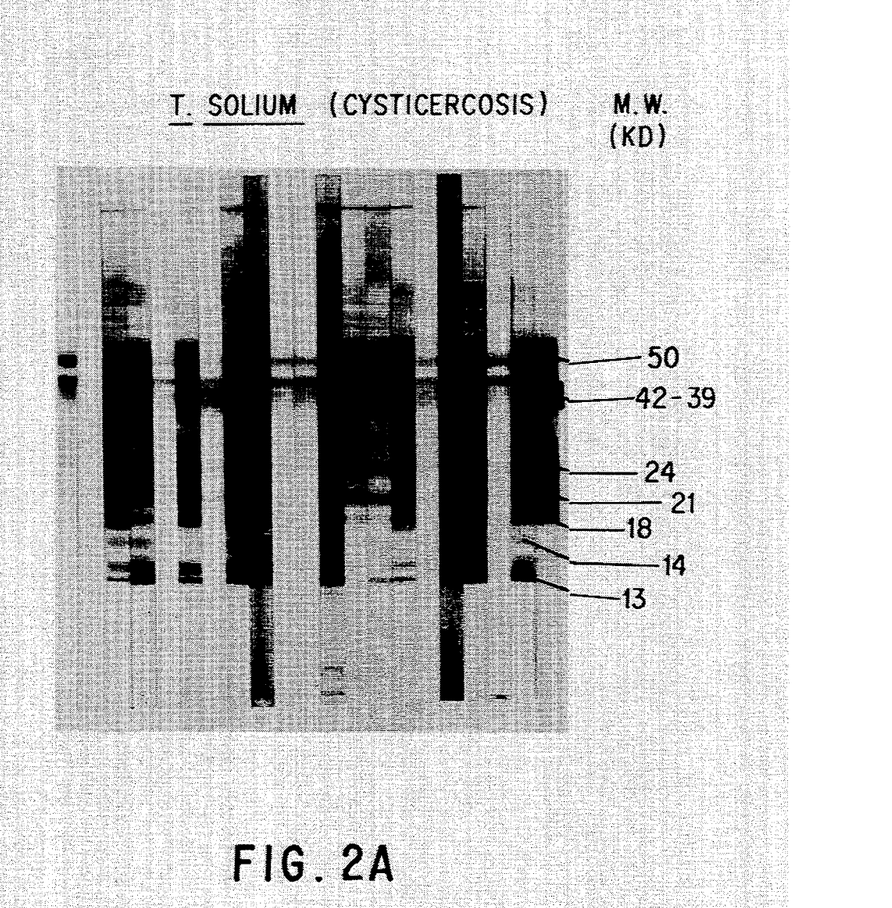
FIGS. 2A and 2B show EITB assay for cysticercosis antibodies. LL-GP was resolved by SDS-PAGE, electroblotted onto nitrocellulose sheets at 20–80 ng/ul per mm, and cut into 3 mm strips. Strips were exposed to 1:50 diluted serum or 1:10 diluted CSF for 1 hr and developed with anti-Ig-POD and substrate (see Materials and Methods for details). 2A=specimens from confirmed cysticercosis cases. Panel 2B=specimens from heterologous infections. The 7 diagnostic glycoprotein bands are marked with their respective molecular weights (KD).

The purification yielded a lentil lectin bound glycoprotein fraction (LL-GP). Typical EITB results with LL-GP for serum from a number of positive cases are shown in FIG. 2A. There are 7 glycoprotein bands commonly recognized by antibodies from serum of cysticercosis cases. These diagnostic bands are: GP50, GP42-39, GP24, GP21, GP18, GP14, AND GP13, respectively. The letters GP signify the glycoprotein nature of these antigens, and the numbers denote their respective molecular weights in K daltons. As is typical of most glycoproteins, these antigens produce rather broad bands in SDS-PAGE. The molecular weights were, therefore, calculated from the middle of each band. A single value was obtained for each antigen except GP42-39, which covers an extraordinarily broad zone: from 39–42 KD. For brevity, this antigen is henceforth referred to as GP42.

A group of 3 sharply focused bands with molecular weights slightly greater than 13 KD are visible just above GP13. These bands, although not counted as specific diagnostic bands, are usually recognized by the antibodies from most cysticercosis cases.

Figure 2B:
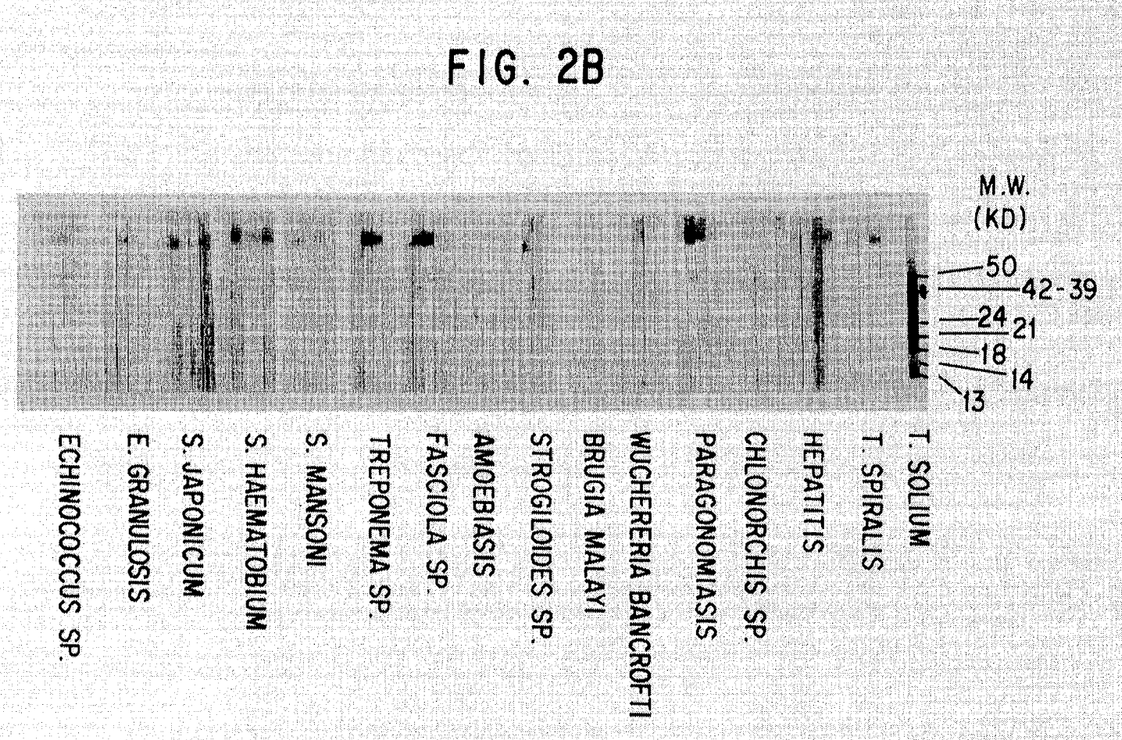

Although LL-GP does contain more components than just the 7 diagnostic bands, most of the other glycoproteins are either nonreactive, or they are located well away from the molecular weight zone occupied by the 7 diagnostic bands. Those sera from Echinococcosis patients which cross-reacted, did so at above 70 KD. As shown by FIG. 2B, most other sera did not show any reaction at all to LL-GP.

Figure 3:
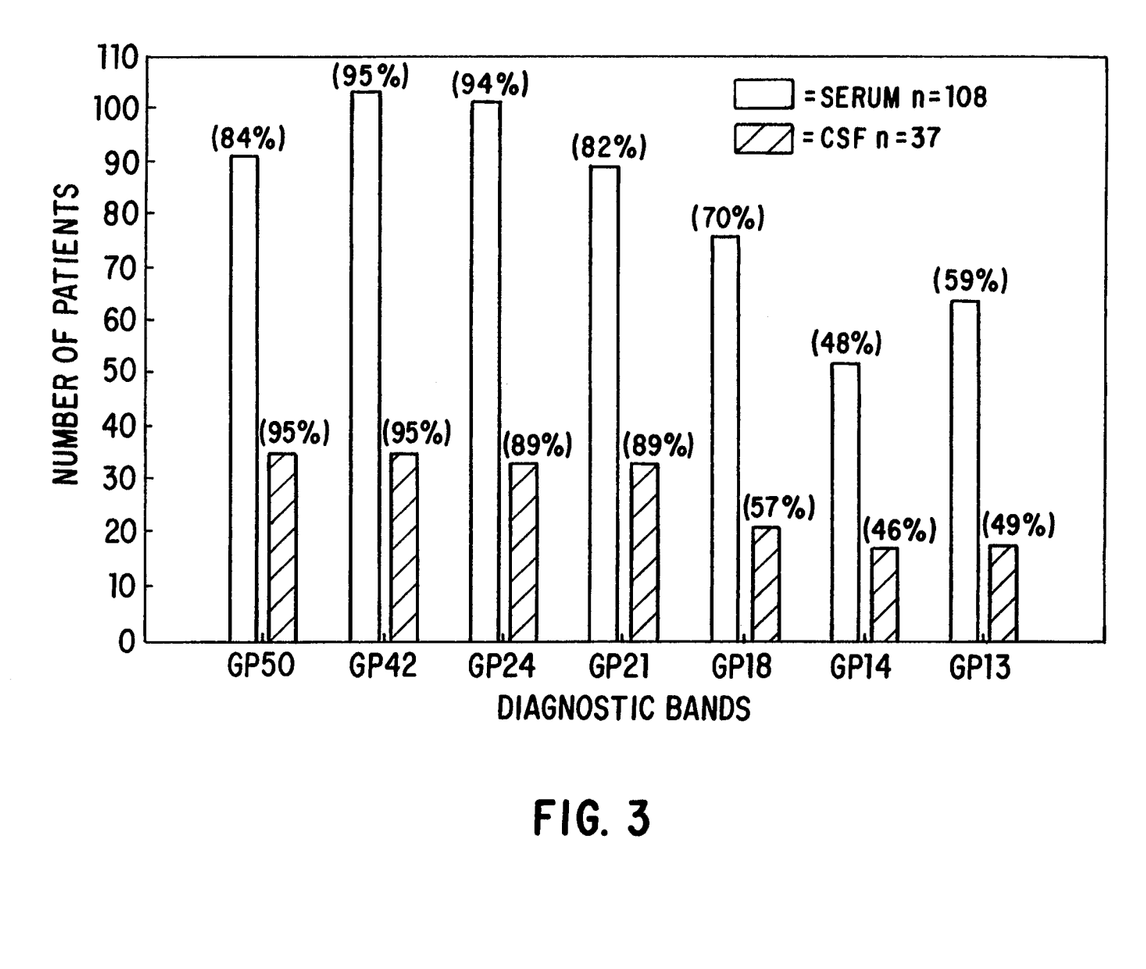
FIG. 3 shows antigen recognition frequencies by antibodies from cysticercosis cases for all individual diagnostic bands. The 7 individual diagnostic bands are identified on the x-axis (GP50–GP13). Serum and CSF samples are accounted for separately and percentages are based their totals.
Figure 4:
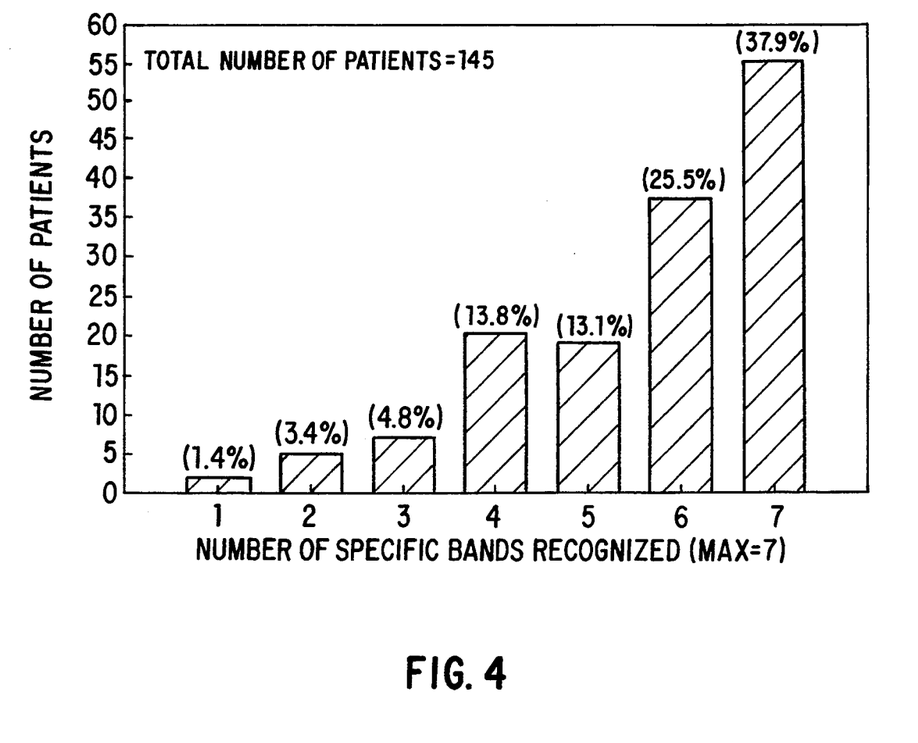
FIG. 4 shows the numbers of diagnostic bands recognized by individual serum or CSF from cysticercosis cases. Data from serum and CSF are combined.

With respect to band recognition frequencies and patterns, as can be seen by FIG. 3, among cysticercosis patients, GP42 and GP24 glycoprotein bands are the most commonly recognized antigens. There is apparently little difference between the recognition patterns of CSF compared to those of serum. Almost all patients react to more than 1 of the diagnostic bands as shown by FIG. 4. Over half of the patients tested reacted to at least 6 out of 7 bands, and almost 40% of the patients recognized all 7 of the diagnostic glycoproteins.

In diagnosing neurocysticercosis, no single band alone is recognized by all of the patients. All 7 of the glycoprotein bands are uniquely specific for cysticercosis. In other words, no other serum showed reaction to any of these 7 diagnostic glycoproteins. Therefor, any reaction to 1 or all of the 7 glycoprotein bands should be considered a positive indication of cysticercosis or at least exposure to *T. solium*.

Through now to assay performance, Table I, listed the EITB results of all specimens from cysticercosis, heterologous infection, and control cases. The present EITB using LL-GP antigens, is an assay with 100% specificity and 98% sensitivity. These values represent a J index of 0.98. the J index is described in Yorden, Cancer; 3:32–35 (1950) which is an art accepted measurement of test performance, gives equal weight to the consideration of sensitivity and specificity, and does not take the prevalence of the disease into consideration.

Another way of expressing test efficacy which does take the prevalence of the disease into account, is to consider the predictive values and efficiencies at various prevalence levels as described by Galen et al., Sensitivity, specificity, predictive value, or efficiency. In: Predictive value and efficiency of medical diagnoses. J. Wiley and Sons, New York, N.Y. 30:1975. At a prevalence of 3%, which is reasonable for the general population of an endemic country, the EITB for cysticercosis will have the following efficacy:

Predictive value of positive tests=100.0%
Predictive value of negative tests=99.9%
Test efficiency=99.94%

At a prevalence of 30%, the expected level for a hospital patient population with abnormal CT/MRI's and neurological symptoms, the test efficacy is as follows:

Predictive value of positive tests=100.0%
Predictive value of negative tests=99.2%
Test efficiency=99.40%

Relationship Between EITB and Cyst Locations

Table II shows the locations of all cysts in confirmed cysticercosis patients. Most cases had parenchymal cysts. Two of the specimens that tested negative came from this category. These two samples were from the same patient. An earlier specimen from this patient was positive. While not being bound to any theory, possibly the two negative sera were from a post treatment period, and antibody to LL-GP was no longer present. We were not able to confirm treatment dates for this patient, and follow-up data were not available. In our confirmed positive test population, multiple samples were available from only 4 patients. All, except the patient mentioned above, had positive EITB's for all of their test samples.

TABLE II
RELATIONSHIP OF EITB REACTIVITY TO CYST LOCATIONS FROM PARASITOLOGICALLY CONFIRMED CASES

| CYST LOCATIONS | NUMBER WITH EITB POSITIVE | WEAK[1] | NEGATIVE | TOTAL NUMBER |
|---|---|---|---|---|
| Ocular | 15 | 0 | 0 | 15 |
| Meningeal | 7 | 0 | 0 | 7 |
| Parenchymal | 71 | 3 | 2 | 76 |
| Intraventricular | 44 | 1 | 0 | 45 |
| Spinal | 14 | 0 | 0 | 14 |
| Subcutaneous | 29 | 3 | 1 | 33 |
| Not specified | 15 | 0 | 0 | 15 |

[1]Weak reaction = only one band recognized, and reaction to it is weak.

The third negative test came from a patient with a single subcutaneous cyst. The pathology report for this patient indicated, with a fair degree of certainty, that it was a *T. solium* cyst. From these low numbers of negative test results, it is difficult to determine whether there is diminished sensitivity with subcutaneous infections.

DISCUSSION

The EITB using LL-GP antigens from *T. solium* cysts is an assay with 100% specificity and 98% sensitivity which represent a significant improvement over previous reports. The efficacy of this assay was based on a test population of 578 cases, 148 with confirmed cysticercosis, 376 from 18 heterologous infections and 54 healthy controls. This assay is equally sensitive for virtually all cyst locations, so it is a viable approach to the diagnosis of cysticercosis. The EITB for human cysticercosis can become essential in managing patients with neurological disorders. Surgical decisions can now be based on confirmatory laboratory data in addition to other medical methodologies for the disease.

Having thus described the invention, it will be apparent to one of ordinary skill in the art that many changes and modifications can be made thereto without departing from the spirit or scope of the invention as set forth herein.

We claim:

1. A method for diagnosing human neurocysticercosis utilizing an immunoblot assay which comprises:
   contacting serum or cerebrospinal fluid of a human to be diagnosed with *Taenia solium* larval glycoprotein antigens, said glycoprotein antigens being identified as GP50, GP42, GP24, GP21, GP18, GP14, and GP13, wherein GP indicates that said antigen is a glycoprotein and the number indicates the molecular weight in kilodaltons as determined by SDS-PAGE under non-reducing conditions after isolation by lentil lectin affinity; and
   detecting the binding of antibody present in said serum or cerebrospinal fluid to at least one of said *Taenia solium* glycoprotein antigens, the presence of binding indicating human neurocysticercosis.

2. A matrix having immobilized thereon larval antigens of *Taenia solium*, said larval antigens having molecular weights of 50 Kd, 42 Kd, 24 Kd, 21 Kd, 18 Kd, 14 Kd and 13 Kd as determined by SDS-PAGE under non-reducing conditions after isolation by lentil lectin affinity.

3. The matrix of claim 2 wherein said matrix is nitrocellulose.

4. The matrix of claim 2 wherein said matrix is nylon.

5. The matrix of claim 2 wherein said matrix is paper.

6. The matrix of claim 2 wherein said matrix is a strip having said antigens immobilized thereon.

7. The matrix of claim 2 wherein said antigens are arranged as separate bands on said matrix.

8. A kit for detecting antibodies to larval antigens of *Taenia solium* which comprises said matrix of claim 2; and a reagent for detecting a reaction between said antigens and antibodies against said antigens.

9. The matrix of claim 6 wherein said strips are in an enclosure that retains moisture.

10. The matrix of claim 7 wherein said strips are in an enclosure that retains moisture.

* * * * *